United States Patent
Wang et al.

(10) Patent No.: US 9,527,963 B2
(45) Date of Patent: Dec. 27, 2016

(54) PROCESS OF PRODUCING AND APPLICATIONS OF A MULTI-COMPONENT BENZO[1,2-B:4,5-B] DIFLUOROTHIENOTHIOPHENE RANDOMLY SUBSTITUTED POLYMERS FOR ORGANIC SOLAR CELLS

(71) Applicants: PHILLIPS 66 COMPANY, Houston, TX (US); SOLARMER ENERGY, INC., El Monte, CA (US)

(72) Inventors: Wei Wang, Arcadia, CA (US); Jun Yang, West Covina, CA (US); Chenjun Shi, La Puente, CA (US); Christopher Daeffler, Pasadena, CA (US); Janice Hawkins, Lake Forest, CA (US); Yue Wu, San Gabriel, CA (US); Ting He, Bartlesville, OK (US); Hui Huang, Beijing (CN); Amit Palkar, Bartlesville, OK (US); Kathy Woody, Bartlesville, OK (US); Joe Bullock, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 14/722,650

(22) Filed: May 27, 2015

(65) Prior Publication Data
US 2015/0344630 A1    Dec. 3, 2015

Related U.S. Application Data

(60) Provisional application No. 62/005,066, filed on May 30, 2014.

(51) Int. Cl.
| | |
|---|---|
| C08G 75/06 | (2006.01) |
| C07D 495/04 | (2006.01) |
| C08G 61/12 | (2006.01) |
| A61K 31/4162 | (2006.01) |
| C07B 59/00 | (2006.01) |

(52) U.S. Cl.
CPC .............. *C08G 75/06* (2013.01); *C07D 495/04* (2013.01); *C08G 61/123* (2013.01); *A61K 31/4162* (2013.01); *C07B 59/002* (2013.01)

(58) Field of Classification Search
CPC ..... C08G 75/06; C08G 61/123; C07D 495/04; A61K 31/4162; C07B 59/002
See application file for complete search history.

(56) References Cited

U.S. PATENT DOCUMENTS

| | | | |
|---|---|---|---|
| 8,436,134 B2 | 5/2013 | Yu et al. | |
| 8,653,228 B2 | 2/2014 | Yu et al. | |
| 8,703,960 B2 | 4/2014 | Huang | |
| 8,895,751 B2 | 11/2014 | Huang | |
| 2012/0279568 A1* | 11/2012 | Choi | H01L 51/0036 136/263 |
| 2013/0056071 A1 | 3/2013 | Palkar et al. | |
| 2013/0214213 A1 | 8/2013 | Wang et al. | |
| 2014/0151657 A1 | 6/2014 | Wang et al. | |
| 2014/0221590 A1 | 8/2014 | Woody et al. | |
| 2015/0136224 A1 | 5/2015 | Shi et al. | |
| 2015/0210800 A1 | 7/2015 | Wang et al. | |

OTHER PUBLICATIONS

USPTO structure search, Mar. 2016.*

* cited by examiner

*Primary Examiner* — Gregory Listvoyb
(74) *Attorney, Agent, or Firm* — Phillips 66 Company

(57) ABSTRACT

A process of dissolving 3-fluoro-4,6-dihydrothieno[3,4-b] thiophene in a solvent to create a solution. An initiator is then added to the solution to produce an initiated solution followed by adding a fluorinated chemical to the initiated solution to produce 2,3-difluoro-4,6-dihydrothieno[3,4-b] thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4-b]thiophene to produce 4,6-dibromo-2,3-difluorothieno[2,3-c]thiophene 4,6-dibromo-2,3-difluorothieno[2,3-c]thiophene is then debrominated and polymerized to

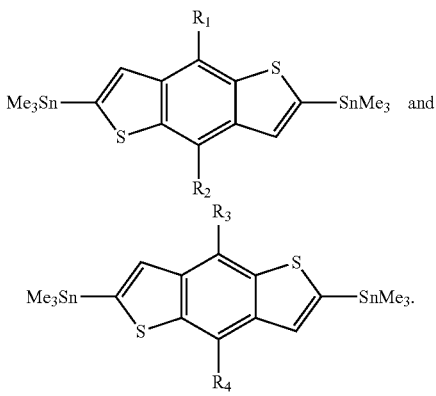

The stoichiometric ratio of (f+g)≈h and f, g and h are not equal to 0. Additionally, in this embodiment R1, R2, R3 and R4 are independently selected from the group consisting of alkyl group, alkoxy group, aryl groups and combinations thereof and where the combination of R1, R2, R3 and R4 are not all identical.

17 Claims, No Drawings

PROCESS OF PRODUCING AND APPLICATIONS OF A MULTI-COMPONENT BENZO[1,2-B:4,5-B] DIFLUOROTHIENOTHIOPHENE RANDOMLY SUBSTITUTED POLYMERS FOR ORGANIC SOLAR CELLS

CROSS-REFERENCE TO RELATED APPLICATIONS

This application is a non-provisional application which claims the benefit of and priority to U.S. Provisional Application Ser. No. 62/005,066 filed May 30, 2014, entitled "Process of Producing and Applications of a Multi-Component Benzo[1,2-B:4,5-B] Difluorothienothiophene Randomly Substituted Polymers for Organic Solar Cells," which is hereby incorporated by reference in its entirety.

STATEMENT REGARDING FEDERALLY SPONSORED RESEARCH OR DEVELOPMENT

None.

FIELD OF THE INVENTION

This invention relates to process of producing and applications for a multi-component benzo[1,2-B:4,5-B]dithiophene-difluorothienothiophene polymer.

BACKGROUND OF THE INVENTION

Solar energy using photovoltaic effect requires active semiconducting materials to convert light into electricity. Currently, solar cells based on silicon are the dominating technology due to their high conversion efficiency. Recently, solar cells based on organic materials showed interesting features, especially on the potential of low cost in materials and processing. Judging from the recent success in organic light emitting diodes based on a reverse effect of photovoltaic effect, organic solar cells are very promising.

Organic photovoltaic cells have many potential advantages when compared to traditional silicon-based devices. Organic photovoltaic cells are light weight, economical in the materials used, and can be deposited on low cost substrates, such as flexible plastic foils. However, organic photovoltaic devices typically have relatively low quantum yield (the ratio of photons absorbed to carrier pairs generated, or electromagnetic radiation to electricity conversion efficiency), being on the order of 1% or less. This is, in part, thought to be due to the second order nature of the intrinsic photoconductive process. That is, carrier generation requires exciton generation, diffusion and ionization. The diffusion length of an exciton is typically much less than the optical absorption length, requiring a trade off between using a thick, and therefore resistive, cell with multiple or highly folded interfaces, or a thin cell with a low optical absorption efficiency.

Conjugated polymers are polymers containing π-electron conjugated units along the main chain. They can be used as active layer materials for some types of photo-electric devices, such as polymer light emitting devices, polymer solar cells, polymer field effect transistors, etc. As polymer solar cell materials, conjugated polymers should possess some properties, such as high mobility, good harvest of sunlight, good processability, and proper molecular energy level. Some conjugated polymers have proven to be good solar cell materials. Conjugated polymers are made of alternating single and double covalent bonds. The conjugated polymers have a δ-bond backbone of intersecting $sp^2$ hybrid orbitals. The $p_z$ orbitals on the carbon atoms overlap with neighboring $p_z$ orbitals to provide π-bonds. The electrons that comprise the π-bonds are delocalized over the whole molecule. These polymers exhibit electronic properties similar to those seen in inorganic semiconductors. The semiconducting properties of the photovoltaic polymers are derived from their delocalized π bonds.

There is a need in the art for polymer solar cells that exhibit increased solar conversion efficiency.

BRIEF SUMMARY OF THE DISCLOSURE

A process of dissolving 3-fluoro-4,6-dihydrothieno[3,4-b]thiophene in a solvent to create a solution. An initiator is then added to the solution to produce an initiated solution followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4-b]thiophene to produce 4,6-dibromo-2,3-difluorothieno[2,3-c]thiophene. 4,6-dibromo-2,3-difluorothieno[2,3-c]thiophene is then debrominated and polymerized to

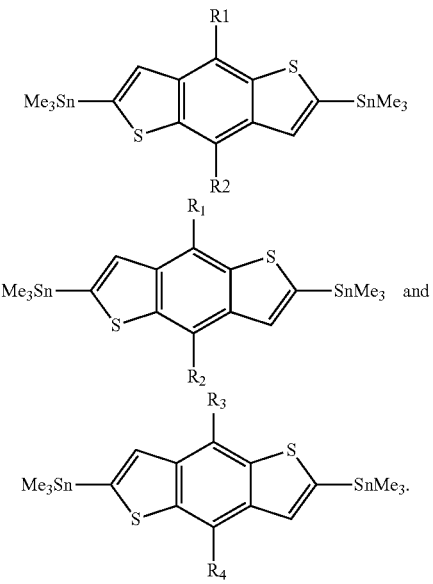

The stoichiometric ratio of (f+g)≈h and f, g and h are not equal to 0. Additionally, in this embodiment R1, R2, R3 and R4 are independently selected from the group consisting of alkyl group, alkoxy group, aryl groups and combinations thereof and where the combination of R1, R2, R3 and R4 are not all identical.

In an alternate embodiment, a process of dissolving 3-fluoro-4,6-dihydrothieno[3,4-b]thiophene in a solvent to create a solution. An initiator is then added to the solution to produce an initiated solution followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4- b]thiophene to produce 4,6-dibromo-2,3-difluorothieno[2,3-c]thiophene. 4,6-dibromo-2,3-difluorothieno[2,3-c]thiophene is then debrominated and polymerized to produce

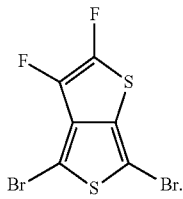

h

Stille coupling is then done to

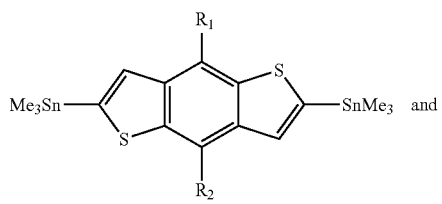

f

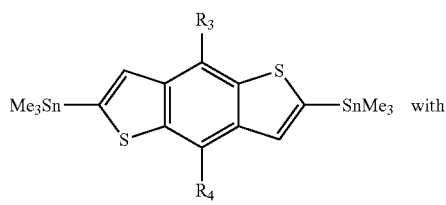

g

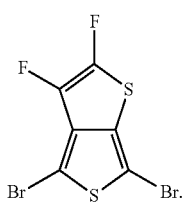

h

The stoichiometric ratio of (f+g)≈h and f, g and h are not equal to 0. Additionally, in this embodiment R1, R2, R3 and R4 are independently selected from the group consisting of alkyl group, alkoxy group, aryl groups and combinations thereof and where the combination of R1, R2, R3 and R4 are not all identical.

BRIEF DESCRIPTION OF THE DRAWINGS

A more complete understanding of the present invention and benefits thereof may be acquired by referring to the follow description taken in conjunction with the accompanying drawings in which:
None.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

"Alkyl," as used herein, refers to an aliphatic hydrocarbon chains. In one embodiment the aliphatic hydrocarbon chains are of 1 to about 100 carbon atoms, preferably 1 to 30 carbon atoms, more preferably, 1 to 20 carbon atoms, and even more preferably, 1 to 10 carbon atoms and includes straight and branched chains such as methyl, ethyl, n-propyl, iso-propyl, n-butyl, isobutyl, sec-butyl, t-butyl, n-pentyl, iso-pentyl, neo-pentyl, n-hexyl, and isohexyl. In this application alkyl groups can include the possibility of substituted and unsubstituted alkyl groups.

"Alkoxy," as used herein, refers to the group R—O— where R is an alkyl group of 1 to 100 carbon atoms. In this application alkoxy groups can include the possibility of substituted and unsubstituted alkoxy groups.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. Aryl groups can be optionally substituted with one or with one or more Rx. In this application aryl groups can include the possibility of substituted aryl groups, bridged aryl groups and fused aryl groups.

The present embodiment describes a process of dissolving 3-fluoro-4,6-dihydrothieno[3,4-b]thiophene in a solvent to create a solution. An initiator is then added to the solution to produce an initiated solution followed by adding a fluorinated chemical to the initiated solution to produce 2,3-difluoro-4,6-dihydrothieno[3,4-b]thiophene. 2,3-difluoro-4,6-dihydrothieno[3,4-b]thiophene is then oxidized with an oxidant to produce 2,3-difluorothieno[3,4-b]thiophene. A brominating step then occurs to the 2,3-difluorothieno[3,4-b]thiophene to produce 4,6-dibromo-2,3-difluorothieno[2,3-c]thiophene. 4,6-dibromo-2,3-difluorothieno[2,3-c]thiophene is then debrominated and polymerized to

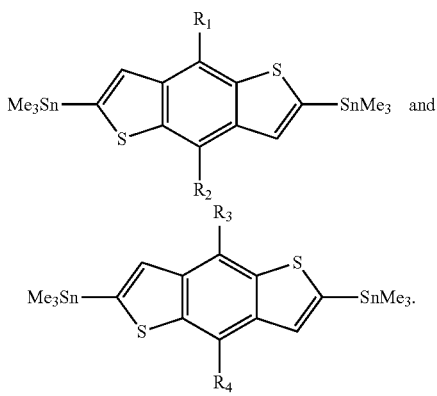

In this embodiment the stoichiometric ratio of (f+g)≈h and f, g and h are not equal to 0. Additionally, in this embodiment R1, R2, R3 and R4 are independently selected from the group consisting of alkyl group, alkoxy group, aryl groups and combinations thereof and where the combination of R1, R2, R3 and R4 are not all identical.

In one embodiment the process produces a conjugated polymer that can be used as a photovoltaic material. In one embodiment the polymerization of f, g and h is regio-regular. In another embodiment the polymerization of f, g and h is regio-random.

In one embodiment, the ratio of

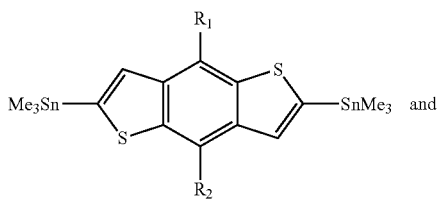

and

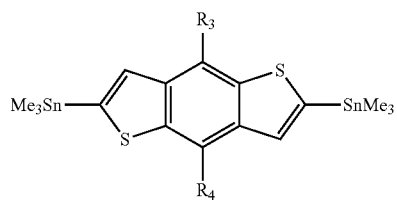

used in the process is around 50:50

In one embodiment different types of polymerization reactions can occur to polymerize

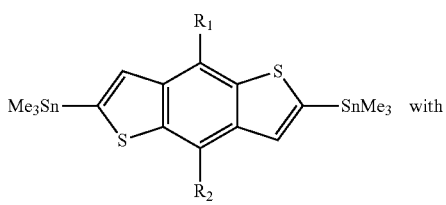

with

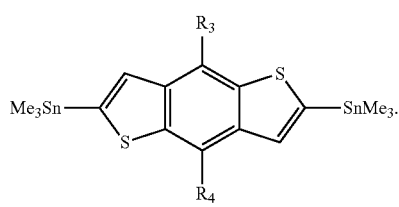

Examples of polymerization reactions that can take place include Stille coupling, Suzuki coupling, Nickel catalyzed and direct arylation.

In an alternate embodiment the solvent used could be tetrahydrofuran

In an alternate embodiment the initiator used could be n-butyllithium

In an alternate embodiment the fluorinated chemical is N-fluorobenzenesulfonimide.

In an alternate embodiment the oxidant is meta-chloroperoxybenzoic acid.

In an alternate embodiment the bromination occurs with N-bromosuccinimide.

In one embodiment the aromatic substituents can comprise of heterocycles and fused heterocycles.

It is theorized that the introduction of the fluorine atom can lower the polymer HOMO energy level and thus will lead to elevated open circuit voltage in photovoltaic devices. The fluorine atom is known to induce better planar molecular conformation in poly-thiophene systems. The formation of a difluorothienothiophene (DFTT) created similar results with better charge transport capability and higher short circuit current and fill factor.

Typically, the number average molecular weight of the polymers is in the range of approximately 1000 to 1,000,000, with ideal polymers having a number average molecular weight in the range of about 5000 to 500,000, and some ideal polymers having a number average molecular weight in the range of approximately 20,000 to 200,000. It will be appreciated that molecular weight can be varied to optimize polymer properties and the inventions of the present disclosure cover all molecular weights. For example, lower molecular weight can ensure solubility, while a higher molecular weight can ensure good film-forming properties.

The polymers produced from the present disclosure can be used as an active layer material or photovoltaic materials in electronic devices or photovoltaic devices such as photodetector devices, solar cell devices, and the like. Photovoltaic devices, including solar cell devices, are generally comprised of laminates of a suitable photovoltaic material between a hole-collecting electrode layer and an electron. In one embodiment the electronic devices are field effect transistors, light emitting devices, and sensors, electrochromic devices and capacitors.

As shown in the examples below the production of a polymer with two different sets of repeat units appears to provide increased performance.

EXAMPLES

List of Acronyms Used

BDT: Benzo[1,2-b:4,5-b']dithiophene
DFTT: 2,3-difluorothieno[3,4-b]thiophene
FTT: 3-Fluorothieno[3,4-b]thiophene
FTT(E): 2-ethylhexyl 3-fluorothieno[3,4-b]thiophene-2-carboxylate
FTT(K1): 2-ethyl-1-(3-fluorothieno[3,4-b]thiophen-2-yl)hexan-1-one
PCE: power conversion efficiency
Jsc: short circuit current
Voc: open circuit voltage
PDI: polydispersity index
$M_n$: number average molecular weight defined by $(\Sigma N_i M_i)/\Sigma N_i$ where Mi is the molecular weight of a chain and Ni is the number of chains of that molecular weight
Soxhlet Extraction: The polymer is washed using a reflux apparatus with different solvents. The solvent and polymer is then heated till the solvent evaporates into a gas, then cools into a liquid. The solvent is then evaporated off and polymer products are produced.

EXAMPLES

Example 1=DFTT (45 mg, 0.135 mmol, 1.0 equiv), FTT(K1) (59.6 mg, 0.135 mmol, 1.0 equiv) and BDT8 (275 mg, 0.270 mmol, 2.0 equiv) were dissolved in a mixture of toluene (10 ml) and DMF (2 ml). The reaction solution was sparged with Ar for 20 minutes. Pd(PPh$_3$)$_4$ (11.0 mg, 4% mol) was added to the reaction mixture, and then sparged with Ar for additional 10 minutes. The solution was heated to 110° C. overnight. The dark blue solution was precipitated into methanol (120 ml) and the solid was collected by filtration. The solid was then dissolved in chloroform and allowed pass through a short column (silica gel). After concentration by roto-vap, the polymer solution was precipitated into hexanes. The solid was collected by centrifugation and dried in vacuum. The product was a dark blue solid (112 mg, 45.2%).

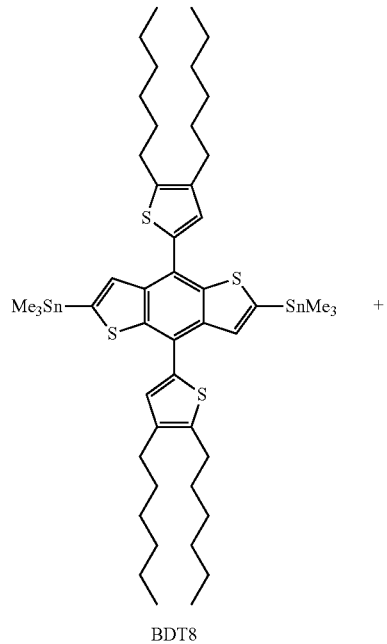

BDT8

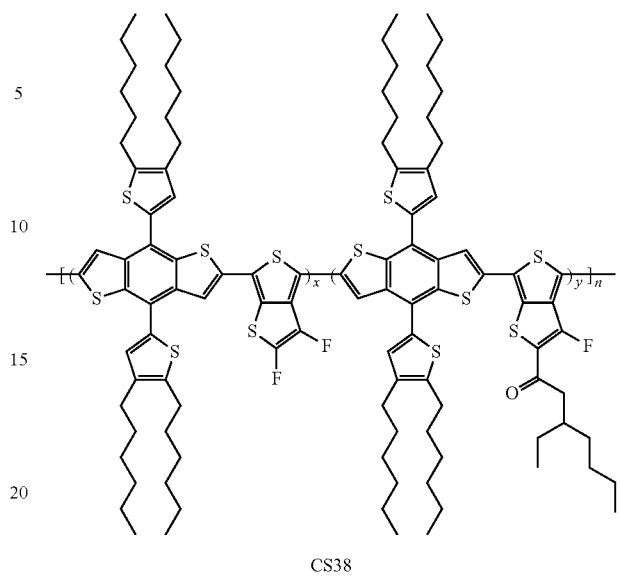

CS38

Example 2=DFTT (50 mg, 0.150 mmol) and BDT8 (152 mg, 0.150 mmol) were dissolved in a mixture of toluene (5 ml) and DMF (1 ml). The reaction solution was sparged with Ar for 20 minutes Pd(PPh$_3$)$_4$ (6.9 mg, 4% mol) was added to the reaction mixture, and then sparged with Ar for an addition 10 minutes. The solution was heated to 110° C. overnight. The dark blue solution was precipitated into methanol (120 ml) and the solid was collected by filtration. The solid was then dissolved in chlorobenzene and allowed to pass through a short column (silica gel). After concentration by roto-vap, the polymer solution was precipitated into hexanes. The solid was collected by centrifugation and dried in vacuum. The product was a dark blue solid (114 mg, 88.45).

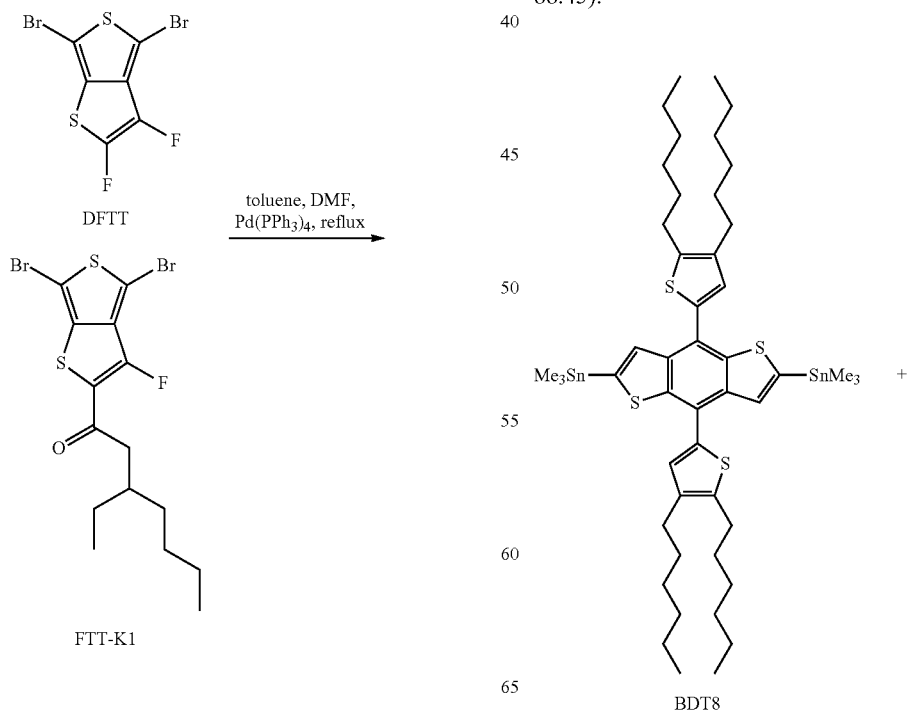

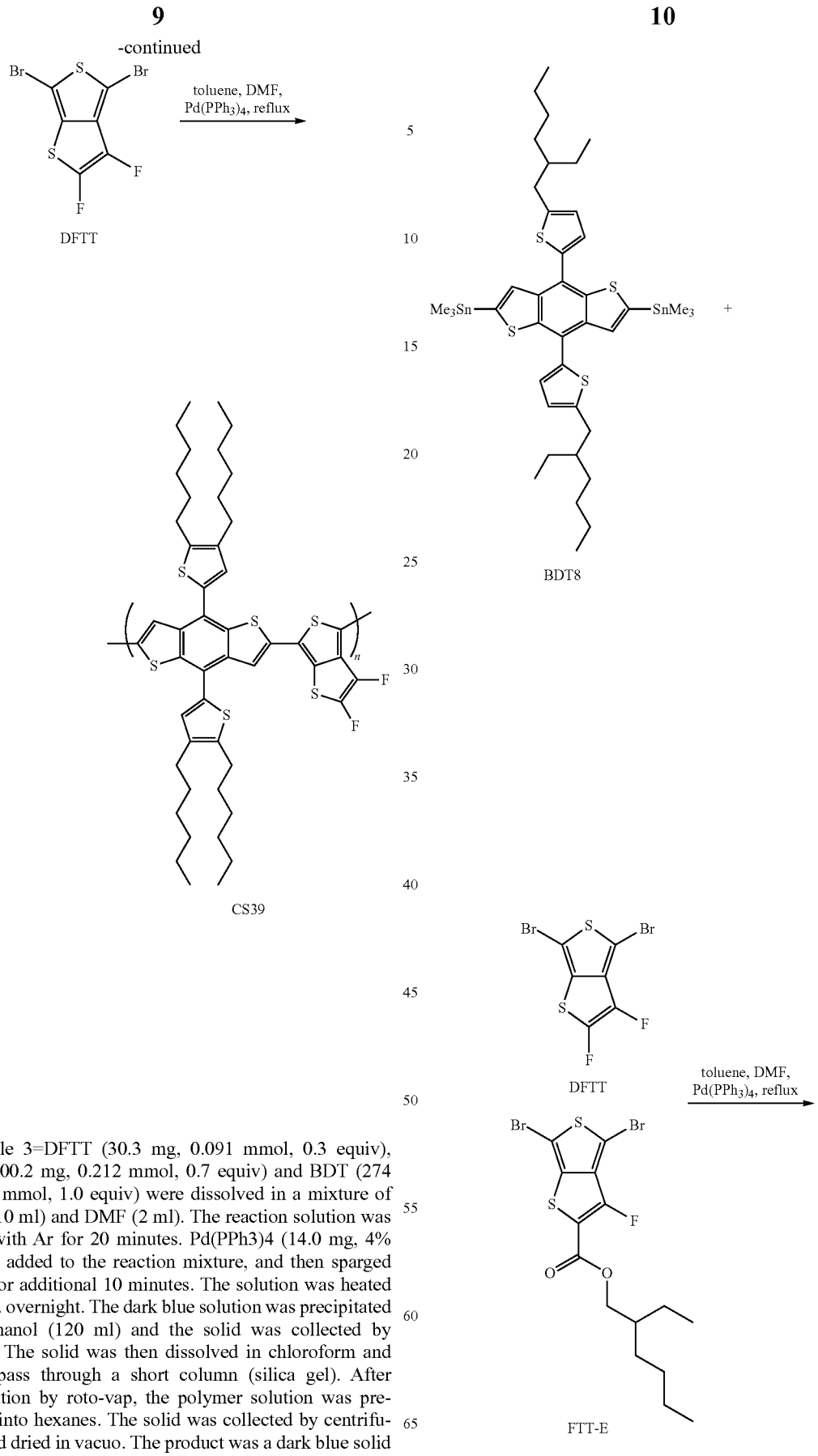

Example 3=DFTT (30.3 mg, 0.091 mmol, 0.3 equiv), FTT-E (100.2 mg, 0.212 mmol, 0.7 equiv) and BDT (274 mg, 0.30 mmol, 1.0 equiv) were dissolved in a mixture of toluene (10 ml) and DMF (2 ml). The reaction solution was sparged with Ar for 20 minutes. Pd(PPh3)4 (14.0 mg, 4% mol) was added to the reaction mixture, and then sparged with Ar for additional 10 minutes. The solution was heated to 110° C. overnight. The dark blue solution was precipitated into methanol (120 ml) and the solid was collected by filtration. The solid was then dissolved in chloroform and allowed pass through a short column (silica gel). After concentration by roto-vap, the polymer solution was precipitated into hexanes. The solid was collected by centrifugation and dried in vacuo. The product was a dark blue solid (238 mg, 92.6%).

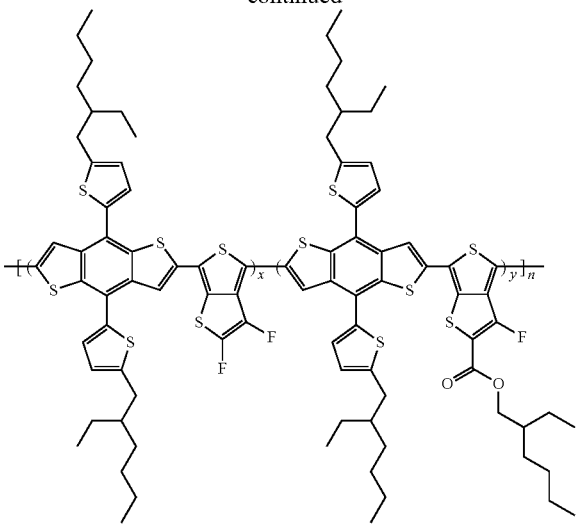

CS42

Device Fabrication and Measurement

Fabrication procedure of a regular device structure (ITO/PEDOT:PSS/active layer/PFN/Al): The polymer and PC$_{70}$BM were dissolved in o-xylene in a 1:1.6 (10 mg mL$_{-1}$: 26 mg mL$_{-1}$, respectively) weight ratios. The solution was stirred at 70° C. overnight, and then filtered using a 2.7 μm glass fiber filter. Prior to use, a 2.5% volume ratio of 1,8-diiodooctane (purchased from Sigma Aldrich) was added to the solution. The solution was left to stir on the hotplate at 70° C. prior to use.

Indium tin oxide (ITO) patterned glass substrates were cleaned by sonication using the following solvents for each step: acetone, detergent water, deionized water, acetone, and isopropanol. Cleaned substrates were left to dry in the oven overnight. Poly(ethylenedioxythiophene):polystyrene sulphonate (PEDOT:PSS) was then spin-coated on ITO/glass substrates at 4000 rpm for 20 s and then annealed at 150° C. for 10 min. The active layer solution was then spin-coated on top of the PEDOT:PSS-coated ITO/glass substrates. The coated samples were left to dry under vacuum for 1 hr. A layer of PFN was deposited prior to electrode deposition. Thermal evaporation was used to deposit the electrode Aluminum (800 Å). The samples were encapsulated prior to removing them from the glove box for testing. The devices with active area of 0.041 cm$_2$ were tested using a 100 mW/cm$_2$ (AM 1.5G) solar simulator.

Inverted structure fabrication: Indium tin oxide (ITO) patterned glass substrates were cleaned by sonication using the following solvents for each step: acetone, detergent water, deionized water, acetone, and isopropanol. Cleaned substrates were left to dry in the oven overnight. ZnO solution (2.5 mg/ml in BuOH) was spin-coated on top of ITO, and thermally annealed at 120° C. for 5 min. The active layer solution was then spin-coated, and the devices were left to dry under vacuum for 1 hr. Thermal evaporation was used to deposit the electrodes: MoO$_3$ 12 nm and Ag 160 nm. The samples were encapsulated prior to removing them from the glove box for testing. The devices with active area of 0.041 cm$_2$ were tested using a 100 mW/cm$_2$ (AM 1.5G) solar simulator.

Table 1 depicts the solar cell performance of polymers from Examples 1-4.

| Polymer | Device Structure | $V_{oc}$ (V) | $J_{sc}$ (mA/cm$^2$) | Fill Factor (%) | PCE (%) |
|---|---|---|---|---|---|
| Example 1 | ITO/PEDOT:PSS/ CS38:PC$_{70}$BM/ PFN/Al | 0.88 | 11.01 | 52.6 | 5.10 |
| Example 2 | ITO/PEDOT:PSS/ CS39:PC$_{70}$BM/ PFN/Al | 0.83 | 11.76 | 62.3 | 6.18 |
| Example 3 | ITO/PEDOT:PSS/ CS42:PC$_{70}$BM/ PFN/Al | 0.74 | 14.12 | 67.4 | 7.12 |

The process of producing a polymer with two different sets of repeat units was combined with a novel DFTT co-monomer.

Example 4=2,3-difluoro-4,6-dihydrothieno[3,4-b]thiophene

An oven-dried, 500 ml flask equipped with a magnetic stir bar was charged with 3-fluoro-4,6-dihydrothieno[3,4-b]thiophene (2.2 g, 13.75 mmol) and anhydrous THF (200 ml) under argon. The solution was cooled at −78° C. under a dry-ice acetone bath. N-butyllithium (2.5 M, 6.0 ml, 1.1 eq) was added dropwise. After cooling at −78° C. for half an hour, the reaction mixture was allowed to warm up to room temperature for 2 hours. The reaction vessel was recooled to −78° C. and (PhSO$_2$)$_2$NF (4.8 g in 80 ml THF) was added dropwise. The mixture was warmed up to room temperature again for another 2 hours. After being quenched with 100 ml water, the organic phase was separated. The aqueous phase was extracted using CH$_2$Cl$_2$. The combined organic phase was dried over anhydrous sodium sulfate. After removal of the solvent, the white solid product was obtained by column chromatography (1.08 g, 44.1% GC-MS found m/q: 178; calculated for C$_6$H$_4$F$_2$S$_2$ 178.22)

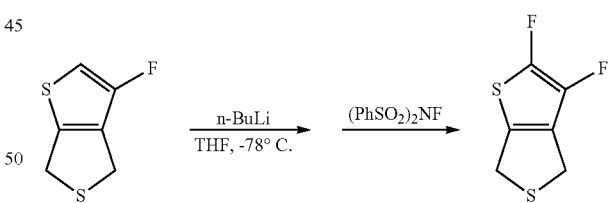

Example 5=2,3-difluorothieno[3,4-b]thiophene

An oven-dried 250 ml flask equipped with a magnetic stir bar was charged with 560 mg of 2,3-difluoro-4,6-dihydrothieno[3,4-b]thiophene (3.15 mmol) and 50 ml methylene chloride. The solution was cooled to 0° C. m-CPBA (0.71 g, 77%, 3.15 mmol) was added to one portion and the reaction mixture was allowed to warm up to room temperature overnight. The solvent was removed by a roto-vap and the residue was redissolved in 15 ml acetic anhydride and heated for 2 hours. The acetic anhydride was then removed by roto-vap and the product was purified by column chromatography to produce 199.5 mg of product. (GC-MS found m/q: 176 (Calculated for C$_6$H$_2$F$_2$S$_2$ 176.21)

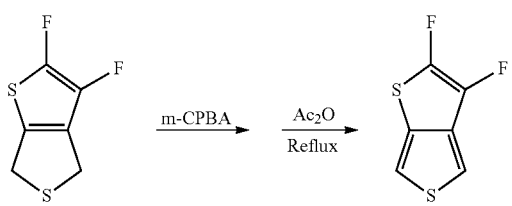 [SMILES: "Ac2O" ; Fc1sc2c(c1F)CSC2 ; "m-CPBA" ; Fc1sc2cscc2c1F]

Example 6=4,6-dibromo-2,3-difluorothieno[2,3-c]thiophene: DFTT 2,3-difluoro-4,6-dihydrothieno[3,4-b]thiophene (195 mg, 1.11 mmol) was dissolved in 10 ml for dry DMF. This solution was cooled at 0° C. In one portion, 592 mg NBS (3.0 eq) was added and the reaction mixture was stirred at 0° C. for 2 hours then warmed up to room temperature overnight. The reaction mixture was then poured into 5% $Na_2S_2O_3$ aqueous solution and extracted with methylene chloride. The organic layer was dried over $Na_2SO_4$. After removal of the solvent, the residue was purified by column chromatography to produce 198 mg (yield 53.5%) of a white solid product. (GC-MS found m/q: 334 (Calculated for $C_6Br_2F_2S_2$ 334.7)

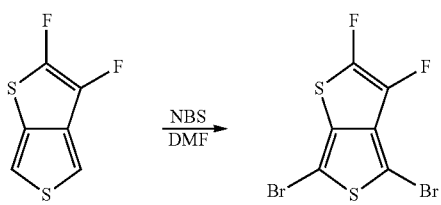

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process comprising:
dissolving 3-fluoro-4,6-dihydrothieno[3,4-b]thiophene in a solvent to create a solution;
adding an initiator to the solution to produce an initiated solution;
adding a fluorinated chemical to the initiated solution to produce 2,3-difluoro-4,6-dihydrothieno[3,4-b]thiophene;
oxidizing 2,3-difluoro-4,6-dihydrothieno[3,4-b]thiophene with an oxidant to produce 2,3-difluorothieno[3,4-b]thiophene;
brominating 2,3-difluorothieno[3,4-b]thiophene to produce 4,6-dibromo-2,3-difluorothieno[2,3-c]thiophene to produce

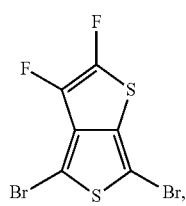

polymerizing

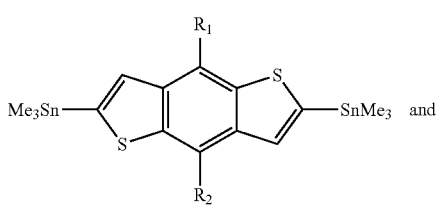

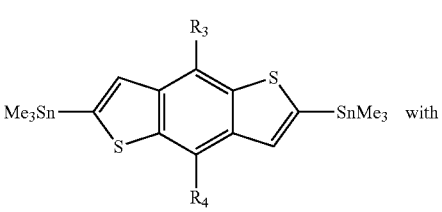

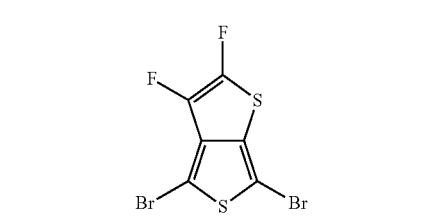

wherein the stoichiometric ratio of (f+g)≈h and f, g and h are not equal to 0; and
wherein R1, R2, R3 and R4 are independently selected from the group consisting of alkyl group, alkoxy group, aryl groups and combinations thereof and where the combination of R1, R2, R3 and R4 are not all identical.

2. The process of claim 1, wherein the solvent is tetrahydrofuran.

3. The process of claim 1, wherein the initiator is n-butyllithium.

4. The process of claim 1, wherein the fluorinated chemical is N-fluorobenzenesulfonimide.

5. The process of claim 1, wherein the oxidant is meta-chloroperoxybenzoic acid.

6. The process of claim 1, wherein the bromination occurs with N-bromosuccinimide.

7. The process of claim 1, wherein the aromatic substituents comprise of heterocycles and fused heterocycles.

8. The process of claim 1, wherein the process produces a conjugated polymer.

9. The process of claim 1, wherein the polymerization of f, g and h is regio-regular.

10. The process of claim 1, wherein the polymerization of f, g and h is regio-random.

11. The process of claim 1, wherein the process produces a photovoltaic material.

12. The process of claim 11, wherein the photovoltaic devices is used as a polymer solar cell device or photodetector device.

13. The process of claim 1, wherein the process produces an active layer material for one or more electronic devices.

14. The process of claim 13, wherein the one or more electronic devices are field effect transistors, light emitting devices, and sensors, electrochromic devices and capacitors.

15. The process of claim 1, wherein the ratio of

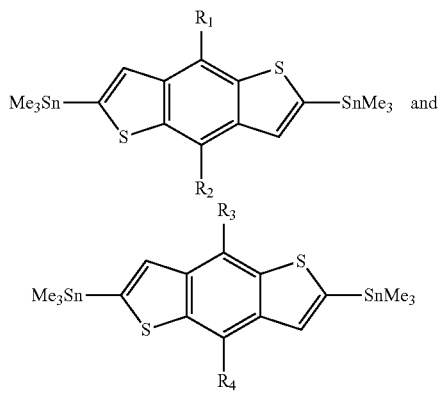

used in the process is around 50:50.

16. The process of claim 1, wherein the polymerizing reaction comprises: stille coupling, suzuki coupling, a nickel catalyzed reaction or direct arylation.

17. A process comprising:
dissolving 3-fluoro-4,6-dihydrothieno[3,4-b]thiophene in a solvent to create a solution;
adding an initiator to the solution to produce an initiated solution;
adding a fluorinated chemical to the initiated solution to produce 2,3-difluoro-4,6-dihydrothieno[3,4-b]thiophene;
oxidizing 2,3-difluoro-4,6-dihydrothieno[3,4-b]thiophene with an oxidant to produce 2,3-difluorothieno[3,4-b]thiophene;
brominating 2,3-difluorothieno[3,4-b]thiophene to produce 4,6-dibromo-2,3-difluorothieno[2,3-c]thiophene to produce

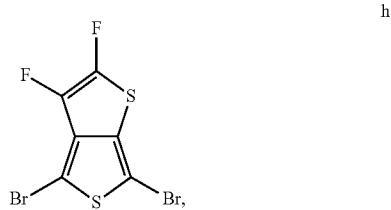

h still coupling

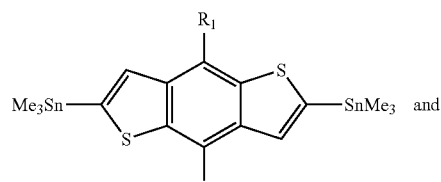

f

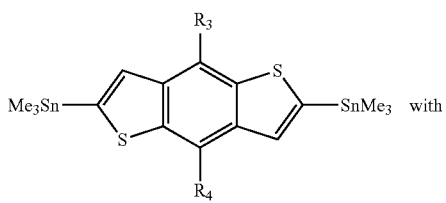

g

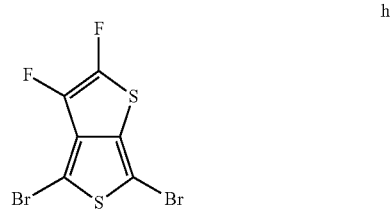 [SMILES: Fc1sc2c(Br)sc(Br)c2c1F]

h wherein the stoichiometric ratio of (f+g)≈h and f, g and h are not equal to 0; and wherein R1, R2, R3 and R4 are independently selected from the group consisting of alkyl group, alkoxy group, aryl groups and combinations thereof and where the combination of R1, R2, R3 and R4 are not all identical.

* * * * *